United States Patent
Hiraku et al.

(10) Patent No.: US 7,063,513 B2
(45) Date of Patent: Jun. 20, 2006

(54) LIQUID CHROMATOGRAPH PUMP WITH DUAL CYLINDERS AND DUAL PLUNGERS

(75) Inventors: Kenji Hiraku, Chiyoda (JP); Kunihiko Takao, Tsuchiura (JP); Hironori Kaji, Hitachinaka (JP); Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/998,937

(22) Filed: Nov. 30, 2004

(65) Prior Publication Data

US 2005/0095145 A1 May 5, 2005

Related U.S. Application Data

(62) Division of application No. 10/608,072, filed on Jun. 30, 2003, now Pat. No. 6,923,916.

(30) Foreign Application Priority Data

Oct. 18, 2002 (JP) ............................. 2002-303697

(51) Int. Cl.
*F04B 3/00* (2006.01)
(52) U.S. Cl. .................... 417/245; 417/254; 417/265; 417/426; 417/44.2
(58) Field of Classification Search ................ 417/245, 417/254, 265, 426, 44.2
See application file for complete search history.

(56) References Cited

U.S. PATENT DOCUMENTS

| | | | | |
|---|---|---|---|---|
| 1,270,493 A | * | 6/1918 | Campodonico | ............. 417/211 |
| 2,274,224 A | * | 2/1942 | Vickers | ....................... 417/250 |
| 2,373,779 A | * | 4/1945 | Ricardo | ....................... 417/265 |
| 4,233,156 A | | 11/1980 | Tsukada | |
| 4,600,365 A | * | 7/1986 | Riggenmann | ............... 417/246 |
| 4,681,513 A | * | 7/1987 | Saito et al. | .................... 417/2 |
| 4,752,385 A | | 6/1988 | Wilson | |
| 4,808,077 A | * | 2/1989 | Kan et al. | ...................... 417/2 |
| 4,810,168 A | * | 3/1989 | Nogami et al. | ................. 417/2 |
| 4,883,409 A | * | 11/1989 | Strohmeier et al. | ........... 417/43 |
| 4,980,059 A | | 12/1990 | Barlow et al. | |
| 5,324,175 A | * | 6/1994 | Sorensen et al. | ........... 417/254 |
| 5,637,208 A | | 6/1997 | Dourdeville | |
| 5,653,876 A | * | 8/1997 | Funke | ..................... 210/198.2 |
| 5,852,231 A | * | 12/1998 | Kaji | .......................... 73/61.56 |
| 5,897,781 A | | 4/1999 | Dourdeville | |
| 6,099,724 A | | 8/2000 | Dourdeville | |

FOREIGN PATENT DOCUMENTS

JP U-63-36668 3/1988

OTHER PUBLICATIONS

PTO Translation 2005-036668, pp. 1-3, Oct. 5, 2004.

* cited by examiner

*Primary Examiner*—Charles G. Freay
*Assistant Examiner*—Emmanuel Sayoc
(74) *Attorney, Agent, or Firm*—Antonelli, Terry, Stout and Kraus, LLP.

(57) ABSTRACT

In a pump for feeding a liquid for chromatography, first and second plungers form first and second volumes respectively together with first and second chambers, the first plunger is prevented from changing the first volume sufficiently for feeding the liquid between the first and second volumes when the second plunger decreases the second volume to discharge the fluid from the second volume to an outlet path of the pump for the chromatography.

21 Claims, 8 Drawing Sheets

LIQUID CHROMATOGRAPH PUMP WITH DUAL CYLINDERS AND DUAL PLUNGERS

CROSS-REFERENCE TO RELATED APPLICATIONS

This application is a division of application Ser. No. 10/608,072 filed on Jun. 30, 2003 now U.S. Pat. No. 6,923,916. The contents of application Ser. No. 10/608,072 are hereby incorporated herein by reference in their entirety.

BACKGROUND OF THE INVENTION

The present invention relates to a pump for feeding a liquid for chromatography and a control method therefor.

In a prior art pump as disclosed JP-U-63-36668, when a first plunger move to put a liquid into the pump, a second plunger move to feed the liquid out of the pump so that a change in flow rate of the liquid discharged from the pump is decreased.

BRIEF SUMMARY OF THE INVENTION

An object of the present invention is to provide a pump for feeding a liquid for chromatography and a control method therefor, by which pump and method a minimal flow rate of the liquid is correctly maintained without a discontinuation of the correctly maintained minimal flow rate of the liquid.

In a pump for feeding a liquid for chromatography, comprising first and second chambers, first and second plungers forming first and second volumes respectively together with the first and second chambers and being capable of reciprocating in the first and second chambers respectively in such a manner that the first and second volumes are variable in accordance with respective movements of the first and second plungers, a communication path connecting fluidly the first and second volumes to each other, an inlet path communicating fluidly with the first volume, from which inlet path the liquid to be fed is capable of being supplied into the first volume, and an outlet path communicating fluidly with the second volume, by which outlet path the liquid to be fed is capable of being discharged from the second volume, according to the present invention, the first plunger is prevented from changing the first volume sufficiently for feeding the liquid between the first volume and the second volume when the second plunger decreases the second volume to discharge the fluid from the second volume to the outlet path for the chromatography.

Since the first plunger is prevented from changing the first volume sufficiently for feeding the liquid between the first volume and the second volume when the second plunger decreases the second volume to discharge the fluid from the second volume to the outlet path for the chromatography, the minimal flow rate of the liquid is correctly maintained without the discontinuation of the correctly maintained minimal flow rate of the liquid.

It is further preferable for correctly maintaining the minimal flow rate of the liquid without the discontinuation of the correctly maintained minimal flow rate of the liquid that the first plunger is prevented from changing the first volume sufficiently for changing a pressure of the liquid in the second volume through the communication path when the second plunger decreases the second volume to discharge the fluid from the second volume to the outlet path for the chromatography.

It is preferable for correctly keeping the pressure in the second chamber stably constant that the communication path connects fluidly the first and second volumes to each other in series so that the liquid to be fed for the chromatography is capable of being fed from the first volume through the communication path to the second volume, the communication path includes a check valve for allowing the liquid to flow from the first volume into the second volume when a pressure in the first volume is higher than a pressure in the second volume and preventing the liquid from flowing from the second volume into the first volume when the pressure in the first volume is not higher than the pressure in the second volume. It is preferable for restraining the discontinuation of the correctly maintained minimal flow rate of the liquid caused by the first plunger movement for decreasing the first volume to compensate the second plunger return movement increasing the second volume that when the second plunger decreases the second volume to discharge the fluid from the second volume to the outlet path for the chromatography, the first plunger is capable of decreasing the first volume to increase the pressure of the liquid in the first volume to more than a pressure in the inlet path (at an upstream side of a check valve in the inlet path) and is prevented from decreasing the first volume sufficiently for increasing the pressure of the liquid in the first volume to more than the pressure in the second chamber. The check valve may allow the liquid to flow from the first volume into the second volume when the pressure in the first volume is more than the pressure in the second volume and a difference in absolute value between the pressure in the first volume and the pressure in the second volume is more than a predetermined value more than zero, and prevent the liquid from flowing from the first volume into the second volume when the pressure in the first volume is not more than a total amount of the pressure in the second volume and the predetermined value. It is preferable for restraining the discontinuation of the correctly maintained minimal flow rate of the liquid caused by the first plunger movement for decreasing the first volume to compensate the second plunger return movement increasing the second volume that the first plunger is prevented from decreasing the first volume sufficiently for increasing the pressure of the liquid in the first volume to more than the total amount of the pressure in the second volume and the predetermined value when the second plunger decreases the second volume to discharge the fluid from the second volume to the outlet path for the chromatography. It is preferable for restraining the discontinuation of the correctly maintained minimal flow rate of the liquid caused by the first plunger movement for decreasing the first volume to compensate the second plunger return movement increasing the second volume that when the second plunger decreases the second volume to discharge the fluid from the second volume to the outlet path for the chromatography, the first plunger is capable of decreasing the first volume to increase the pressure of the liquid in the first volume to more than a pressure in the inlet path (at an upstream side of a check valve in the inlet path) and is prevented from decreasing the first volume sufficiently for increasing the pressure of the liquid in the first volume to more than the total amount of the pressure in the second volume and the predetermined value. When the second plunger decreases the second volume to discharge the fluid from the second volume to the outlet path for the chromatography, the first plunger may decrease the first volume to increase the pressure of the liquid in the first volume to more than the pressure in the second volume and is prevented from decreasing the first volume sufficiently for increasing the pressure of the liquid in the first volume to more than the total amount of the pressure in the second volume and the predetermined value.

When the second plunger increases the second volume, the first plunger decreases the first volume sufficiently for feeding the liquid from the first volume into the second volume so that the flow of the liquid discharged from the pump is maintained. The movement of at least one of the first and second plungers (that is, a relative movement between the first and second plungers) should be controlled in such a manner that a difference between a difference (in absolute value) between the increasing rate (per time) of the second volume increased by the second plunger and the decreasing rate (per time) of the volume of the first volume decreased by the first plunger and a predetermined degree is kept within an acceptable range. For keeping the flow rate of the liquid discharged from the pump desirably, it is preferable that the decreasing rate (per time) in absolute value of the first volume decreased by the first plunger is more than the increasing rate (per time) in absolute value of the second volume increased by the second plunger, and the movement of at least one of the first and second plungers (that is, the relative movement between the first and second plungers) is controlled in such a manner that a difference between a difference in absolute value between an increasing rate (per time) of the second volume increased by the second plunger and a decreasing rate (per time) of the volume of the first volume decreased by the first plunger and a desired flow rate of the liquid to be discharged from the second volume to the outlet path for the chromatography is kept within a predetermined range.

For rapidly discharging a gaseous bubble out of the pump and securely preventing the discontinuation of the correctly maintained minimal flow rate of the liquid, it is preferable that a change rate (per time) in absolute value of the first volume with respect to a movement velocity in absolute value of the first plunger is larger than a change rate (per time) in absolute value of the second volume with respect to a movement velocity in absolute value of the second plunger. For keeping the minimal flow rate of the liquid correctly, it is preferable that the first plunger is capable of being stationary at least temporarily when the second plunger decreases the second volume to discharge the fluid from the second volume to the outlet path for the chromatography.

The outlet path may include a drain valve openable to discharge a gas out of the outlet path through the drain valve to fill the outlet path with the liquid when the first plunger decreases the first volume, and closable to discharge the fluid from the second volume out of the pump through the outlet path for the chromatography when the second plunger decreases the second volume. It is preferable for rapidly discharging the bubble out of the pump and securely compensating the second plunger return movement increasing the second volume that a maximum change rate in absolute value of the first volume obtainable in accordance with (with respect to) the movement of the first plunger is larger than a maximum change rate in absolute value of the second volume obtainable in accordance with (with respect to) the movement of the second plunger, and a minimum change rate in absolute value of the first volume obtainable in accordance with (with respect to) the movement of the first plunger is smaller than the maximum change rate in absolute value of the second volume obtainable in accordance with (with respect to) the movement of the second plunger. For minimizing an adverse effect caused by the second plunger return movement increasing the second volume, that a movement velocity in absolute value of the second plunger for increasing the second volume is larger than a movement velocity in absolute value of the second plunger for decreasing the second volume to discharge the fluid from the second volume to the outlet path for the chromatography.

It is preferable for minimize the change of pressure in the second chamber on switching from the decrease of the second volume to the increase of the second chamber that the first plunger is capable of decreasing the first volume to increase a pressure in the first volume when the second plunger decreases the second volume, that is, before switching from the decrease of the second volume to the increase of the second chamber, and/or that the first plunger is capable of decreasing the first volume to pressurize the fluid in the first volume to a pressure insufficient for feeding the liquid from the first volume into the second volume and not more than a desired pressure of the liquid to be discharged from the pump, when the second plunger decreases the second volume, that is, before switching from the decrease of the second volume to the increase of the second chamber.

A method for controlling a pump for feeding a liquid for chromatography, including, first and second chambers, first and second plungers forming first and second volumes respectively together with the first and second chambers and being capable of reciprocating in the first and second chambers respectively in such a manner that the first and second volumes are variable in accordance with respective movements of the first and second plungers, a communication path connecting fluidly the first and second volumes to each other, an inlet path communicating fluidly with the first volume, from which inlet path the liquid to be fed is capable of being supplied into the first volume, and an outlet path communicating fluidly with the second volume, by which outlet path the liquid to be fed is capable of being discharged from the second volume, comprises the steps of:

opening a drain valve in the outlet path to discharge a gas out of the outlet path through the drain valve so that the outlet path is filled with the liquid when the first plunger decreases the first volume, closing the drain valve when the second plunger decreases the second volume to discharge the fluid from the second volume to the outlet path for the chromatography, and controlling at least one of the movement of the first plunger for decreasing the first volume sufficiently for feeding the liquid from the first volume into the second volume and the movement of the second plunger for increasing the second volume (that is, a relative movement between the first and second plungers) in such a manner that a difference between a difference in absolute value between an increasing rate (per time) of the second volume increased by the second plunger and a decreasing rate (per time) of the volume of the first volume decreased by the first plunger and a desired flow rate of the liquid to be discharged from the second volume to the outlet path for the chromatography is kept within a predetermined range.

Other objects, features and advantages of the invention will become apparent from the following description of the embodiments of the invention taken in conjunction with the accompanying drawings.

DETAILED DESCRIPTION OF THE INVENTION

Figure 1:
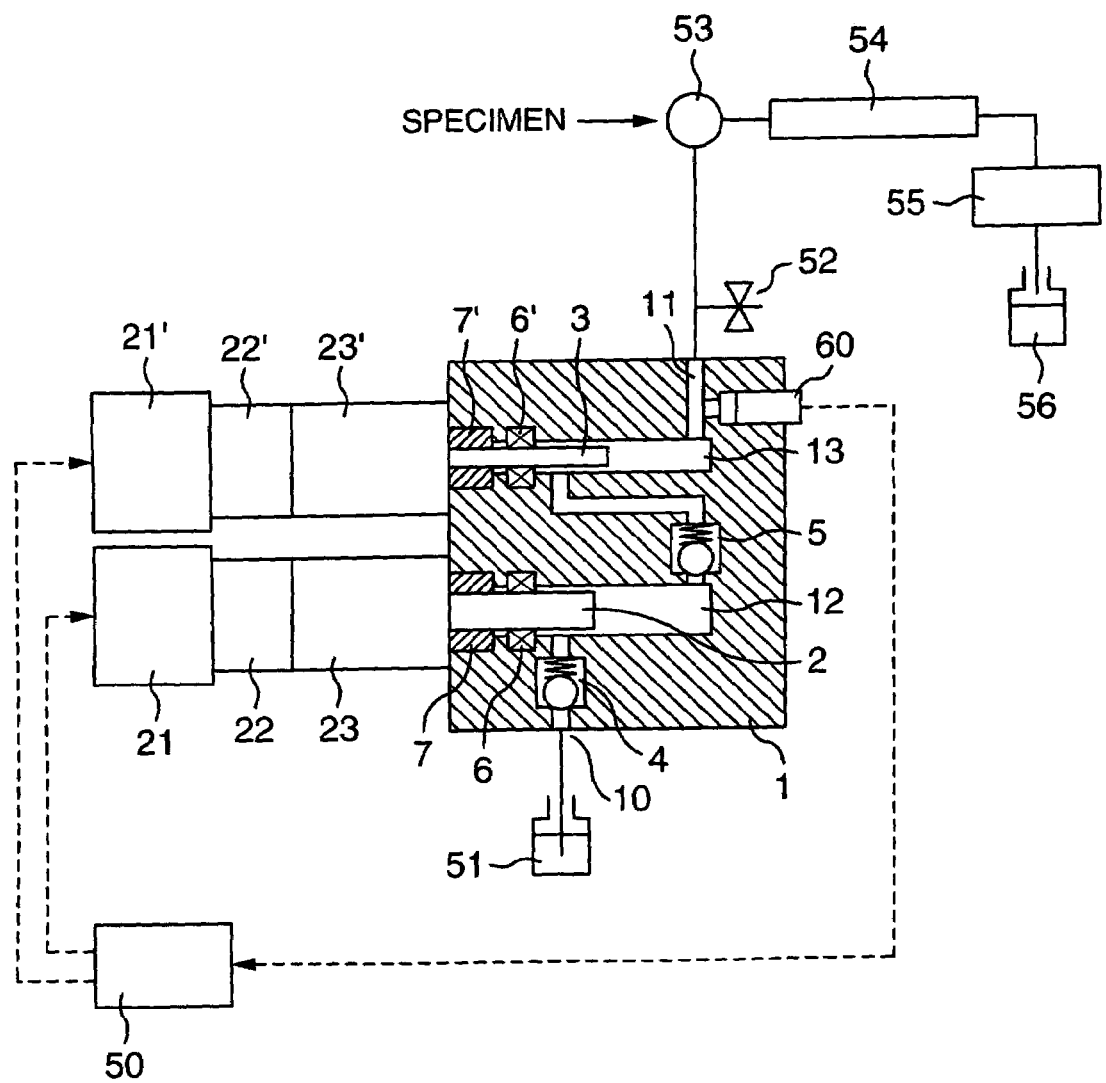
FIG. 1 is a partially cross-sectional view showing a pump of the invention.
Figure 2:
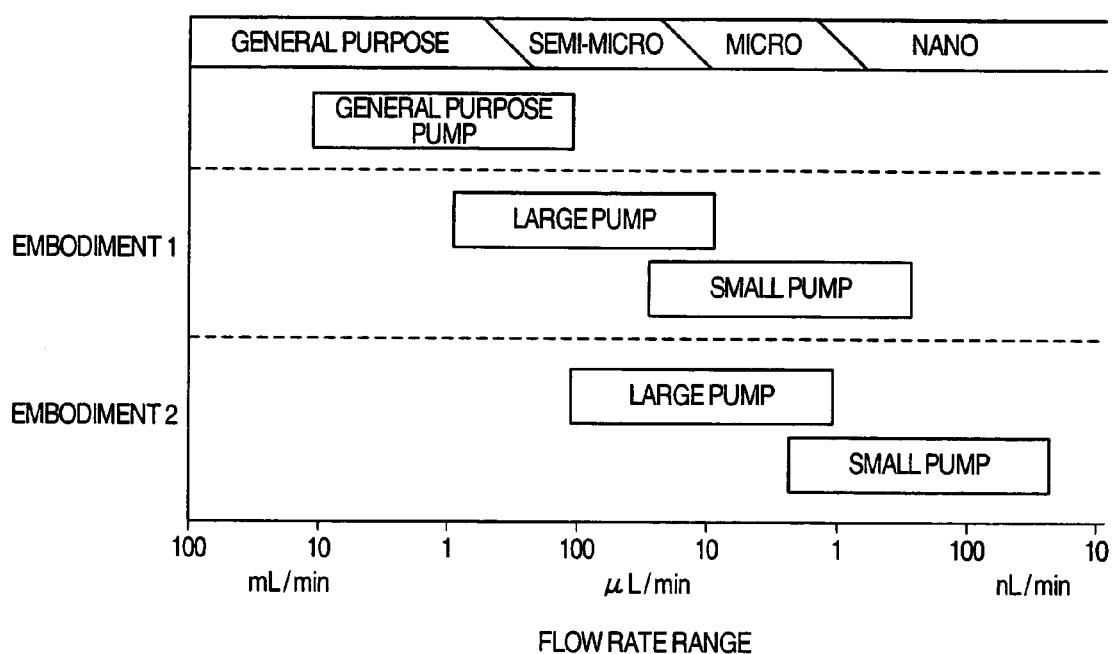
FIG. 2 is a diagram showing pairs of large pump flow rate ranges and small pump flow rate ranges of embodiments of the invention.
Figure 3:
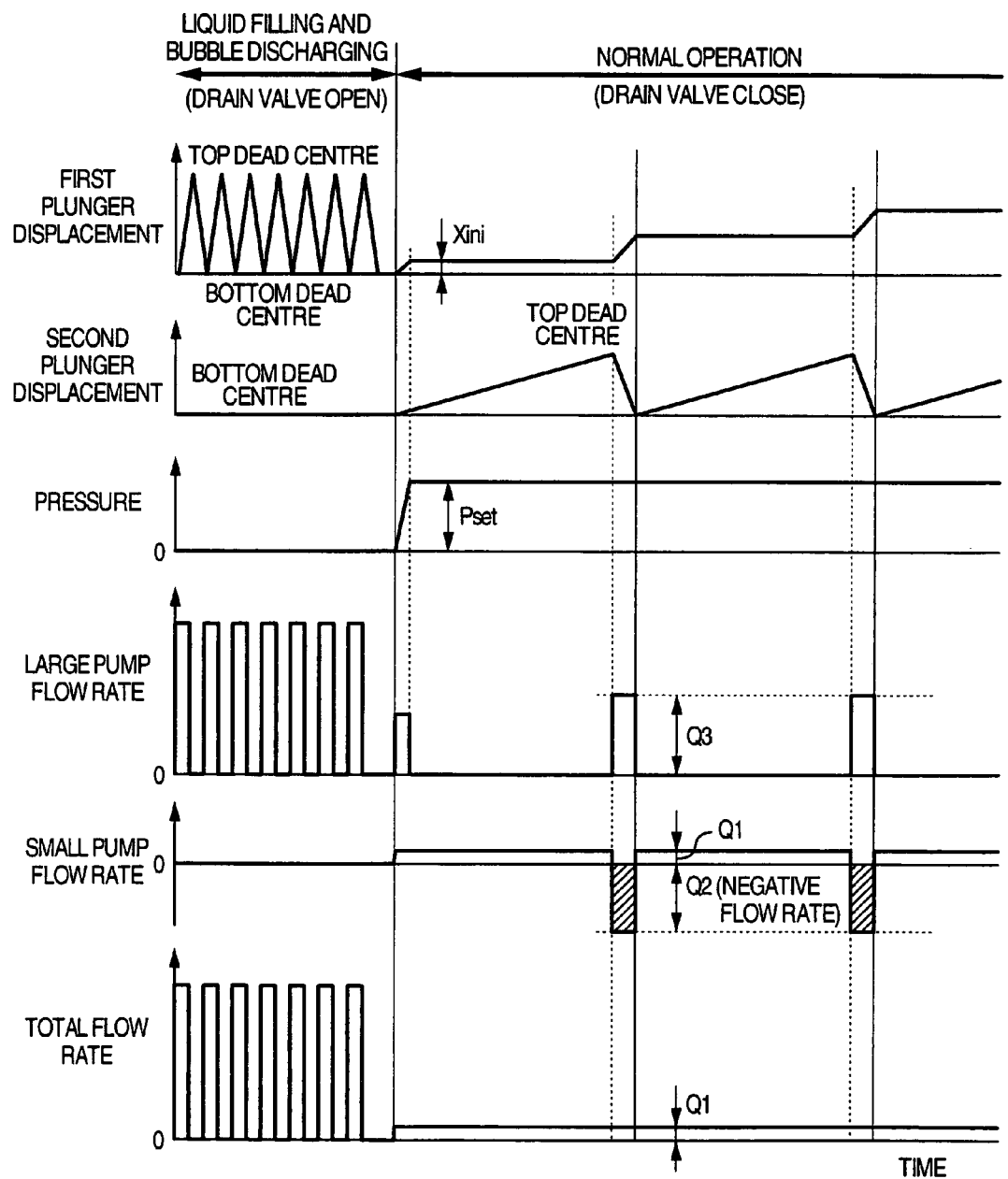
FIG. 3 includes diagrams showing a relationship among operations in a pump of the invention, time proceeding and conditions in the pump.

In an embodiment as shown in FIGS. 1–3, an inlet path 10, an outlet path 11, a first chamber 12 and a second chamber 13 are formed in a pump body 1. First and second plungers 2 and 3 are supported by slide bearings 7 and 7' respectively to be movable in the first and second chambers 12 and 13 respectively. The inlet path 10 for supplying a fluid into the first chamber 12 includes an inlet check valve 4, and a communication path communicating fluidly with the first and second chambers 12 and 13 includes a discharge check valve 5. In each of the check valves 4 and 5, a movable member is pressed against a valve seat by a spring so that a fluidal flow from a fluid tank 51 into the first chamber 12 or from the first chamber 12 into the second chamber 13 is allowed when a fluidal pressure at an upstream side of the check valve is more than a total amount of a fluidal pressure at a downstream side of the check valve and a fluidal pressure caused by the spring, and is prevented when the fluidal pressure at the upstream side of the check valve is not more than the total amount of the fluidal pressure at the downstream side of the check valve and the fluidal pressure caused by the spring. The first plunger 2 is driven linearly by a rotational motor 21 through a reduction gearbox 22 and a rotary-motion and linear motion converter 23, and the second plunger 3 is driven linearly by a rotational motor 21' through a reduction gearbox 22' and a rotary-motion and linear motion converter 23'. Seals 6 and 6' hermetically seal volumes formed respectively by a combination of the first plunger 2 and chamber 12 and a combination of the second plunger 3 and chamber 13 while the first and second plungers 2 and 3 are movable through the seal 6 and 6' respectively. A controller 50 generates control signals for the motors 21 and 21' on the basis of an output signal of a pressure sensor 60.

A solvent 51 is supplied into a pump through the inlet path 10, and discharged from the outlet path 11 to be mixed with a specimen supplied by an injector 53. A solution as a mixture of the solvent 51 and the specimen proceeds through a column 54 so that the specimen is divided to components thereof for componential analysis in a detector 55. The column 54 includes silica-gel particulate through which the solution proceeds, so that a pressure loss of, for example, about 10 MPa is generated across the column 54.

A large (flow rate) pump is formed by the first chamber 12 and plunger 2 and a driving mechanism therefor, and a small (flow rate) pump is formed by the second chamber 13 and plunger 3 and a driving mechanism therefor.

As shown in FIG. 2, the pump according to the invention may generate an extremely small flow rate of, for example, less than 1 mL/min or 1 µL/min. A ratio between a maximum obtainable flow rate and a minimum obtainable flow rate in generally known pumps is 1:100. Therefore, the pump for the extremely small flow rate cannot generate a flow rate sufficient for filling rapidly with the fluid a fluidal line through the pump and an analysis system at the downstream side of the pump, and for discharging rapidly gaseous bubble out of the pump. A desired flow rate is not obtainable correctly when the gaseous bubble exists in the fluidal line.

In the embodiments of the invention, the small pump generates the extremely small flow rate for analysis and the large pump generates the large flow rate for filling the fluidal line with the fluid and for discharging the gaseous bubble out of the pump before the analysis.

The obtainable minimum flow rate of the large pump is smaller than the obtainable maximum flow rate of the small pump, and the obtainable maximum flow rate of the large pump is larger than the obtainable maximum flow rate of the small pump. The flow rate is determined as a product of a cross sectional area of the plunger and a velocity of the plunger. The total flow rate along an abscissa axis in FIG. 2 is a total flow rate obtainable for a high pressure gradient pump operation in which a required maximum flow rate is from several dozen times to several hundred times of a required minimum flow rate. Therefore, a required minimum limit of resolution in flow rate of the pump is less than one tenth or hundredth of the required maximum flow rate.

In an operation of the first embodiment as shown in FIG. 3, before starting the liquid feed of the extremely small flow rate for the analysis, a drain valve 52 is opened and the first plunger 2 reciprocates at a high frequency to generate a large flow rate of the liquid so that the gaseous bubble in the pump and the feel line is discharged therefrom and the pump and feed line are filled with the liquid. Since the large pump is arranged at the upstream side of the small pump so that the liquid supplied from the inlet path 10 flows from the large pump into the small pump to be discharged from the outlet path 11, the bubble can be easily discharged from the second chamber 2 to the outlet path 11. Further, since the liquid is supplied into each of the first and second chambers 12 and 13 at the vicinity of the seal 6, 6' and is discharged from each of the first and second chambers 12 and 13 at the vicinity of a stroke front end of the plunger 2, 3, the liquid flows without a flow stagnation through each of the first and second chambers 12 and 13. When the first plunger reciprocates to discharge the bubble from the pump and feed line, the second plunger 3 is prevented from moving.

During the liquid feed of the extremely small flow rate for the analysis, the drain valve 52 is closed, the first plunger 2 is prevented from moving and the second plunger 3 moves at a low velocity to decrease the second volume so that the liquid is discharged from the pump at the extremely small flow rate. In response to that the second plunger 3 reaches the stroke front end thereof, the second plunger 3 returns to a stroke back end thereof at an obtainable maximum velocity and the first plunger 2 moves to decrease the first volume so that the liquid is discharged from the first chamber 12 into the second chamber to keep a constant flow rate to be discharged from the second chamber 13 to the outlet path 11, that is, a total amount of a negative flow rate or volume increasing rate Q2 of the second chamber 13 and a flow rate or volume decreasing rate Q3 of the first chamber 12 is kept at a desired constant flow rate Q1 to be discharged from the pump. Since the obtainable minimum flow rate of the large pump is smaller than the obtainable maximum flow rate of the small pump, the flow rate or volume decreasing rate Q3 of the first chamber 12 can compensate the negative flow rate or volume increasing rate Q2 of the second chamber 13 while the desired flow rate Q1 to be discharged from the pump is maintained, when the second plunger 3 returns to the stroke back end thereof. Since the second plunger 3 returns to the stroke back end thereof at the obtainable maximum velocity, the obtainable minimum flow rate of the large pump can be large so that the obtainable maximum flow rate of the large pump can be large.

It is preferable for increasing a pressure in the pump to a desired pressure Pset that the first plunger 2 moves by Xini as shown FIG. 3 to decrease the first volume to pressurize the pressure in the pump to the desired pressure. If the pressure in the pump is increased to the desired pressure Pset by only the movement of the second plunger 3, the stroke of the second plunger 3 needs to be large and a time period for reaching the desired pressure Pset needs to be long.

In response to that the first plunger 2 reaches to the vicinity of the stroke front end thereof after a plurality of times of reciprocating movements of the second plunger 13 so that a distance or remaining available stroke between a position of the first plunger 2 and the stroke front end thereof becomes insufficient for keeping the desired constant flow rate Q1 to be discharged from the pump through the return movement of the second plunger 3 to the stroke back end thereof, the first plunger 2 returns to a stroke back end thereof while the second plunger 3 moves to decrease the second chamber for keeping the desired constant flow rate Q1 to be discharged from the pump.

Figure 4:
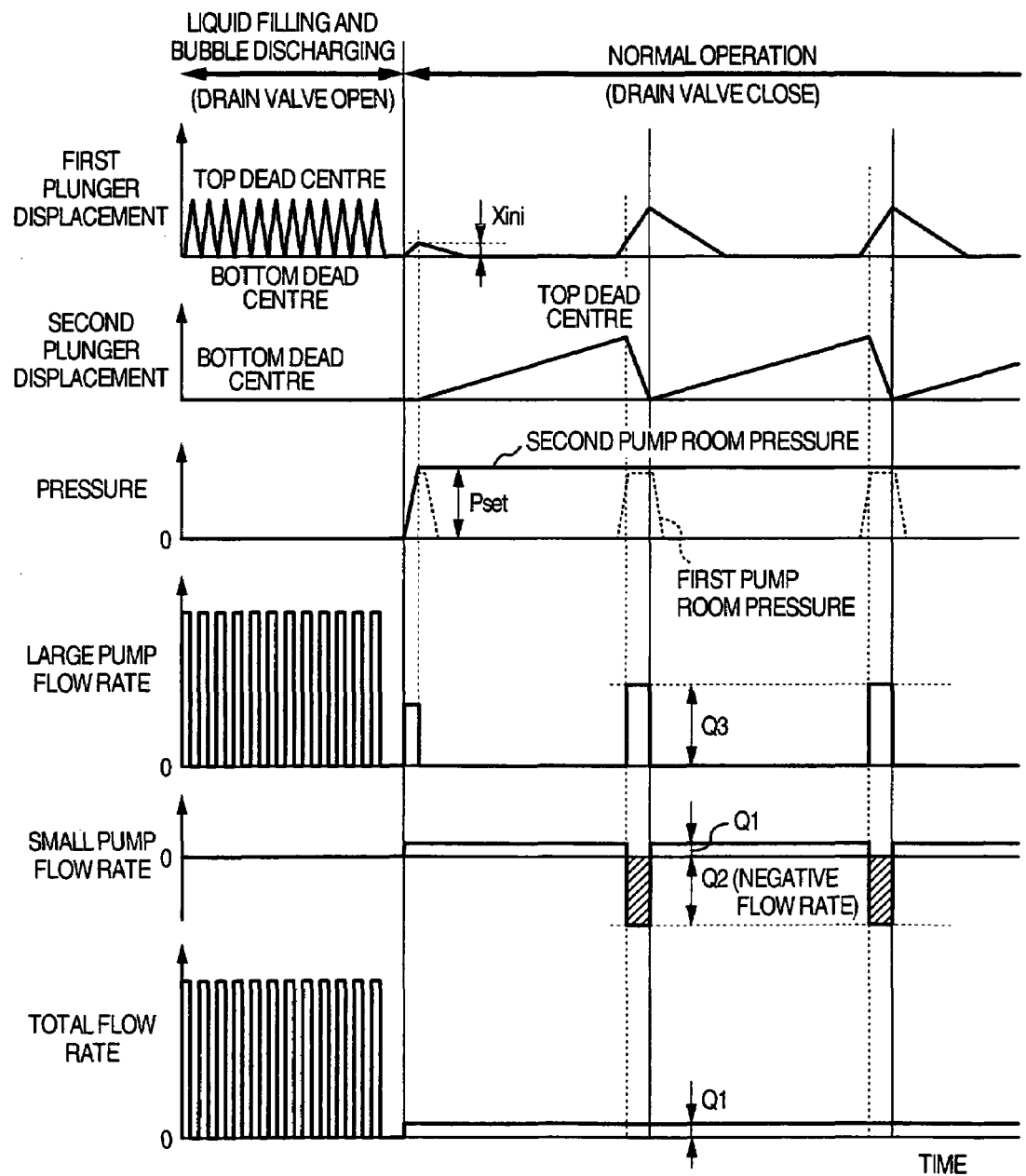
FIG. 4 is includes diagrams showing a relationship among operations in another pump of the invention, time proceeding and conditions in the another pump.

As shown in FIG. 4, the first plunger 2 may return to the stroke back end thereof at each forward stroke of the second plunger 3 in which stroke the second plunger 3 moves to decrease the second chamber for keeping the desired constant flow rate Q1 to be discharged from the pump. In this case, a distance between the stroke front and back ends of the first plunger 2 may be small and the first volume may be small. When the second plunger 3 decreases the second volume to discharge the liquid out of the second volume just before the second plunger 3 returns toward the stroke back end thereof to increase the second volume, the first plunger 2 moves to decrease the first volume so that a difference in pressure between the first and second chamber is decreased to minimize a change of pressure in the second chamber.

Figure 5:
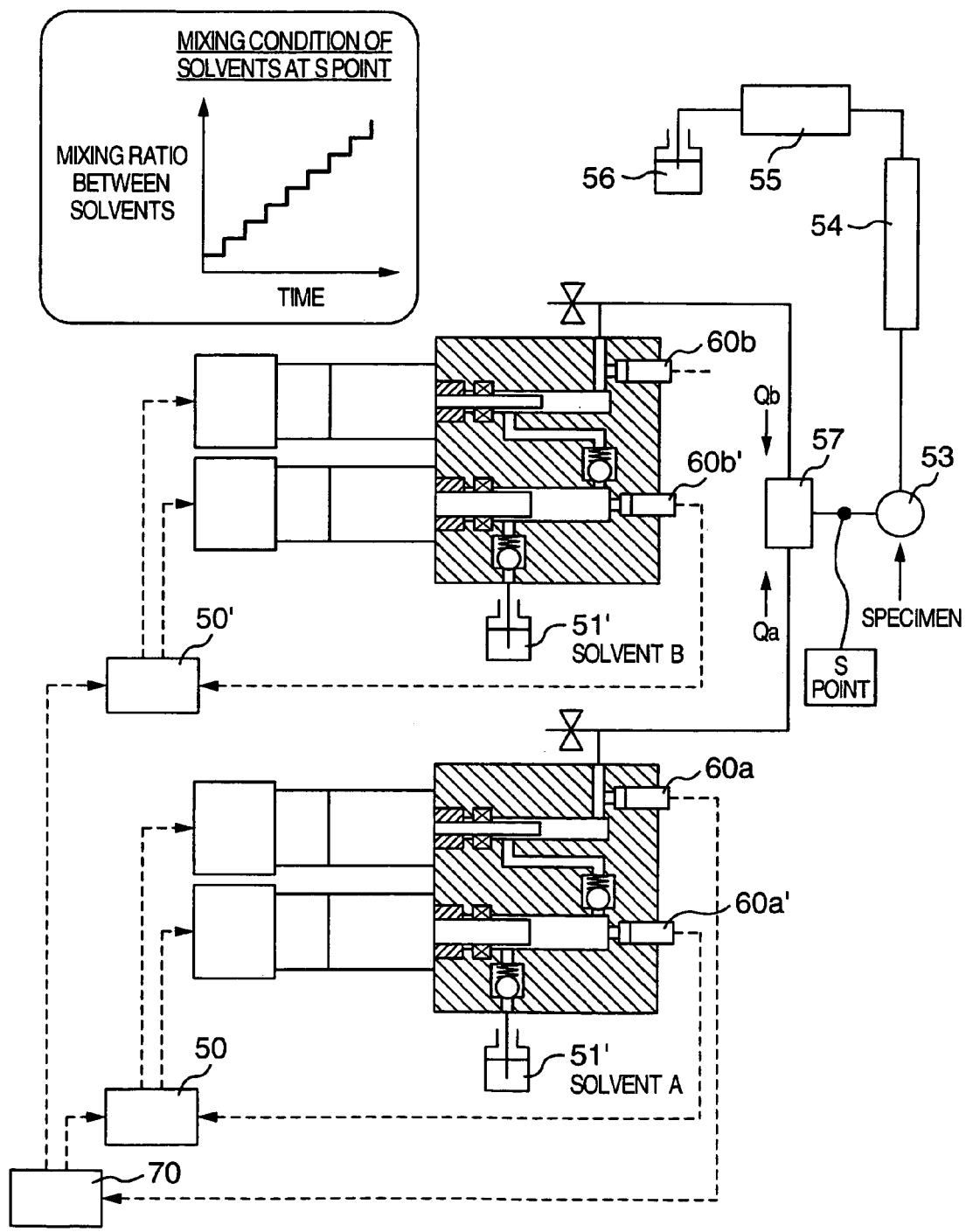
FIG. 5 is a partially cross-sectional view showing a liquid mixing and feeding system in which the pumps of the invention are used.
Figure 6:
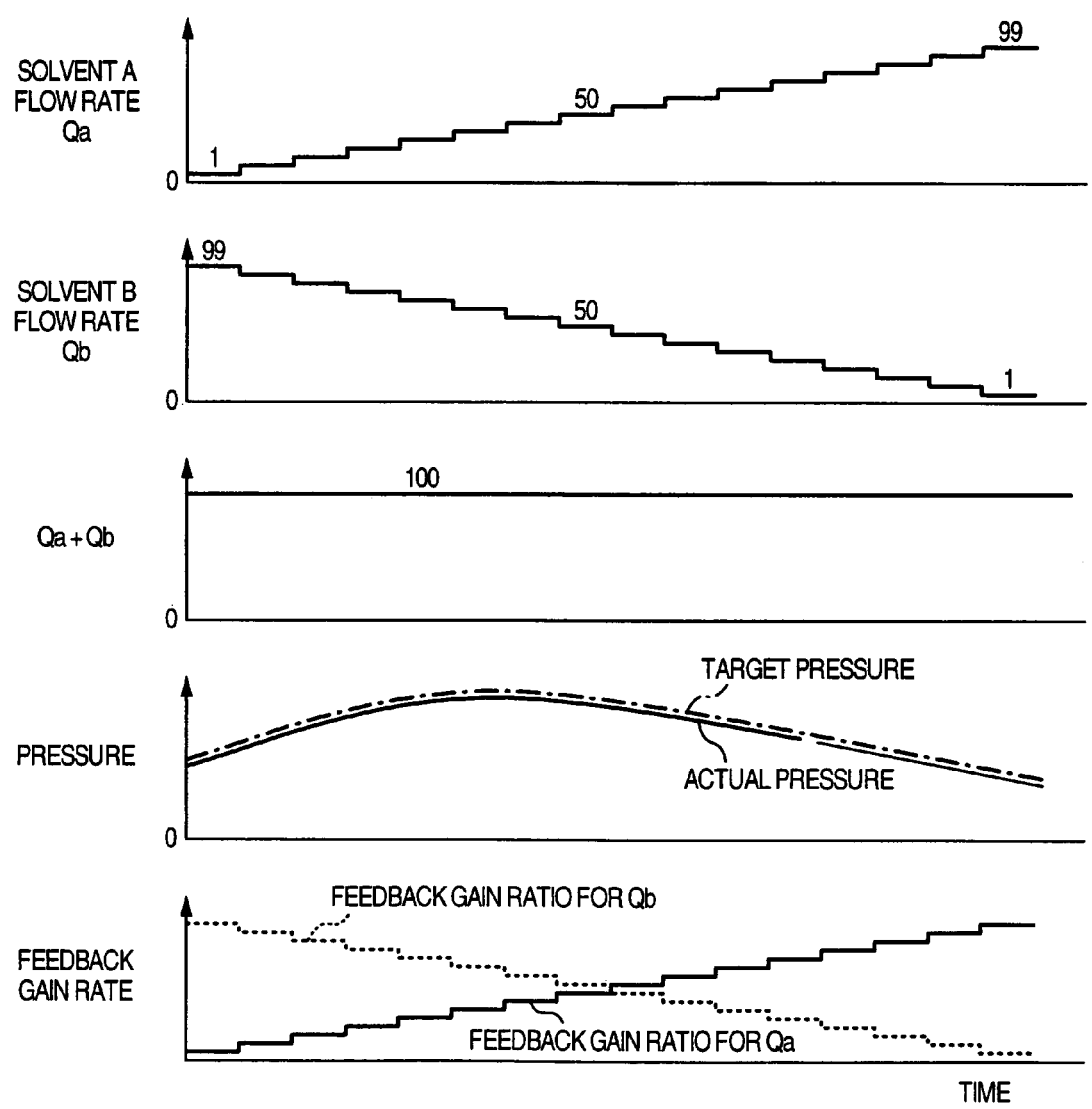
FIG. 6 is includes diagrams showing another relationship among operations in the pump, time proceeding and conditions in the pump.

As shown in FIG. 5, a high-pressure gradient system for changing a mixing ratio between solutions A and B gradually stepwise by adjusting a ratio between flow rates Qa and Qb of the solutions A and B while a total amount of the flow rates Qa and Qb is kept constant may be formed a pair of the pumps of the invention. The ratio between the flow rates Qa and Qb of the solutions A and B is changed from 1:99 to 99:1, as shown in FIG. 6. When the total amount Of the flow rates Qa and Qb is 1 μL/min, a correctly obtainable minimum flow rate, or minimum limit of resolution of each of the flow rates Qa and Qb is 10 nL/min of one hundredth of 1 μL/min is required as a correctly obtainable minimum flow rate, or minimum limit of resolution of each of the flow rates Qa and Qb. If the flow rate discharged from the pump is kept constant, an outlet pressure of the liquid discharged from the outlet path 11 changes in accordance with a change of the mixing ratio, because a fluidal resistance of the column 54 changes in accordance with the change of the mixing ratio.

A relationship between the mixing ratio and the outlet pressure of the liquid obtained when the flow rate discharged from the pump is kept constant is measurable experimentally. Therefore, the change of the outlet pressure of the liquid or a desired outlet pressure of the liquid in accordance with the change of the mixing ratio necessary when the flow rate discharged from the pump is kept constant can be estimated. When an actual outlet pressure of the pump is adjusted by a feedback control at the desired outlet pressure of the liquid necessary when the flow rate discharged from the pump is kept constant, the flow rate discharged from the pump is kept correctly constant. As shown in FIG. 5, an output signal of a pressure sensor 60a or 60b corresponding to the actual outlet pressures of the pumps is input to a main controller 70 so that the pump controllers 60 and 60' controls the pumps to generate the desired outlet pressure of the liquid.

When the actual outlet pressure of the pump is lower than the desired outlet pressure of the liquid, that is, an actual total amount of the flow rates Qa and Qb is lower than the desired total amount of the flow rates Qa and Qb, feedback gains for controlling the flow rates Qa and Qb respectively are adjusted in accordance with the ratio between the flow rates Qa and Qb. For example, when the ratio between the flow rates Qa and Qb is 20:80, the feedback gain for the flow rate Qa is $(20/100) \times K$ (numerical constant), and the feedback gain for the flow rate Qb is $(80/100) \times K$. When the actual total amount of the flow rates Qa and Qb is smaller than the desired total amount of the flow rates Qa and Qb by 5, an ordered value for the flow rate Qa is $20+(20/100) \times K \times 5$, and an ordered value for the flow rate Qb is $80+(80/100) \times K \times 5$.

Since the outlet pressure of each of the pumps varies in accordance with a time proceeding, the pressure in the first volume of each of the pumps needs to change in accordance with the change of the outlet pressure of each of the pumps. In order to prevent the liquid from flowing from the second volume into the first volume, the movement of the first plunger 12 is controlled by the feed back control on the basis of comparison between each of the pressures measured by the sensors 60a' and 60b' and the pressure measured by the sensor 60a in such a manner that the pressure in the first volume of each of the pumps is not more than the pressure in the second volume of the each of the pumps.

Figure 7:
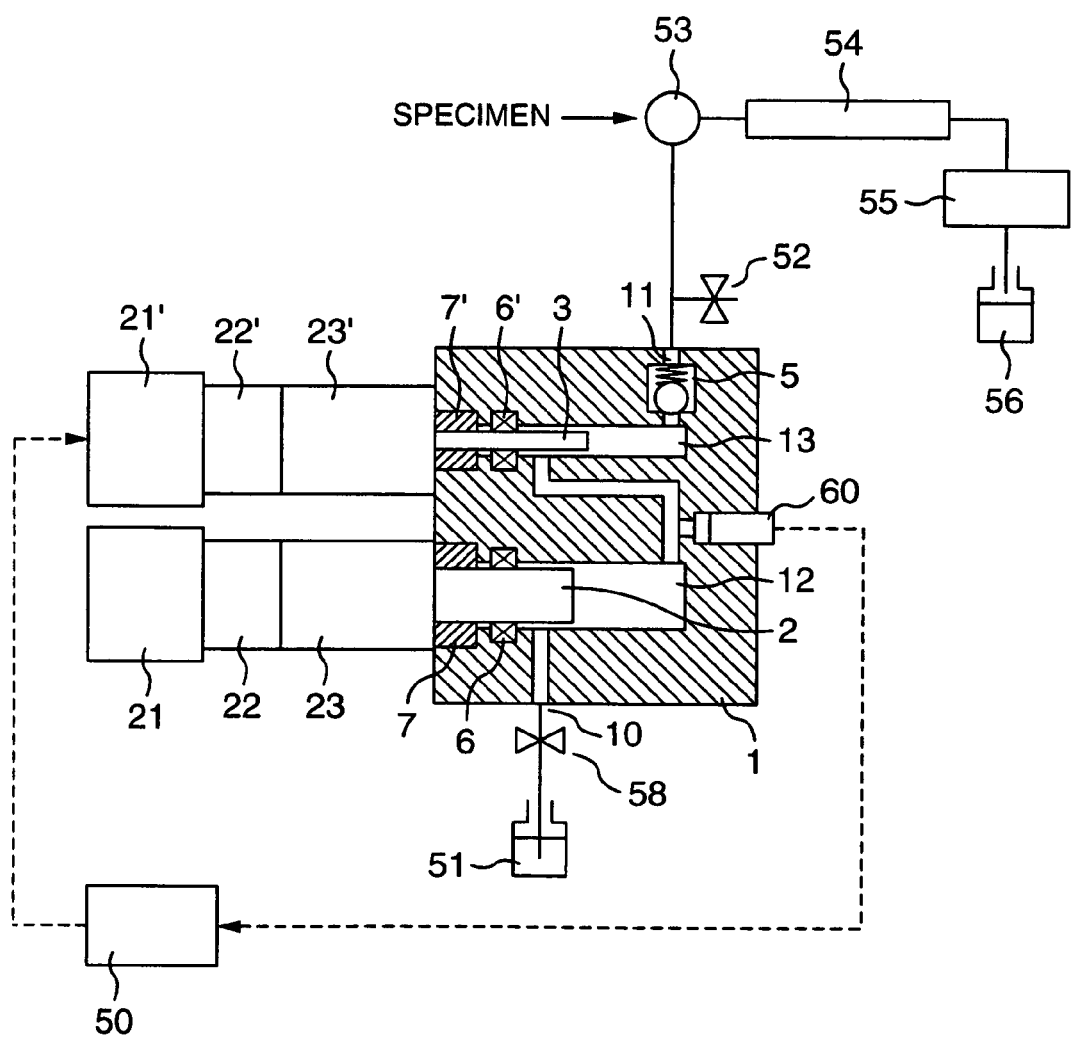
FIG. 7 is a partially cross-sectional view showing a liquid mixing and feeding system in which the pumps of the invention are used.
Figure 8:
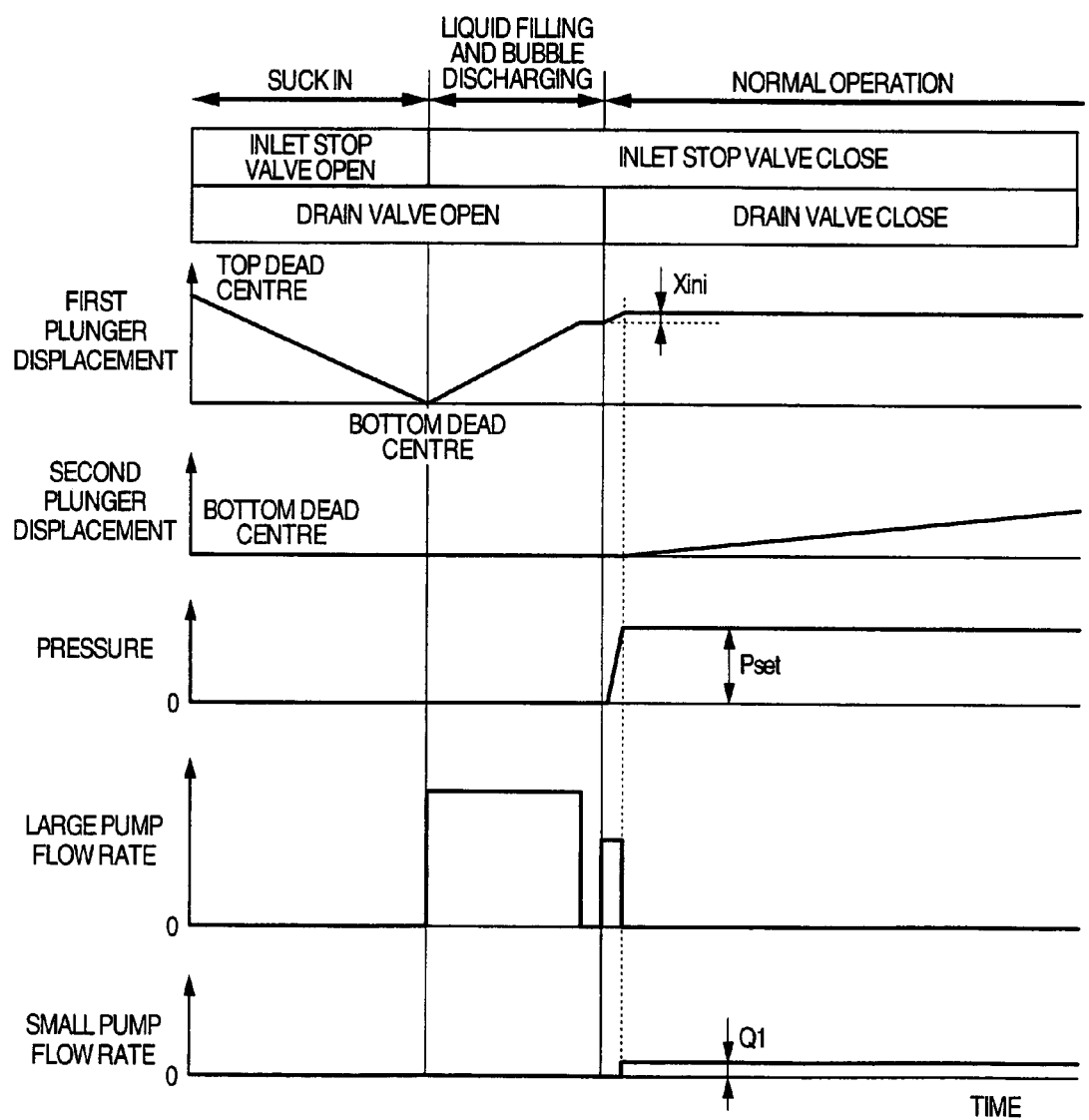
FIG. 8 is includes diagrams showing another relationship among operations in the pump, time proceeding and conditions in the pump.

As shown in FIG. 7, the check valve 4 may be replaced by a shutoff valve 58 in the inlet path 10, and the check valve 5 may be arranged in the outlet path 11 instead of the communication path. In this embodiment, as shown in FIG. 8, the first plunger 2 does not compensate the increase of the second volume by the return stroke of the second plunger 3 toward the back stroke end thereof to keep the pressure in the outlet path 11 constant during the return stroke of the second plunger 3. Before feeding the liquid for the analysis, the first plunger 2 is positioned at the front stroke end thereof and the second plunger 3 is positioned at the back stroke end thereof while the shutoff valve 58 and the drain valve 52 are opened. Thereafter, the first plunger 2 is returned to the back stroke end thereof to take the solution 51 into the first chamber while the second plunger 3 is stationary. After the first plunger 2 reaches the back stroke end thereof, the shutoff valve 58 is closed. Subsequently, the first plunger 2 is moved toward the front stroke end thereof to decrease the first volume so that the gaseous bubble is discharged out of the pump from the drain valve 52. Before the first plunger 2 reaches the front stroke end thereof, the drain valve 52 is closed and the first plunger 2 is stopped. Subsequently, the first plunger 2 moves by the distance Xini to decrease the first volume so that the liquid in the first and second volumes is pressurized to the predetermined pressure Pset. Whie the first plunger is kept stationary, the second plunger 3 moves toward the front stroke end thereof to decrease the second volume to feed the liquid at the flow rate Q1.

The second plunger 3 may be driven to change the second volume by a piezoelectric actuator or a thermal expansion metallic actuator. The first and second chambers 12 and 13 may be arranged in respective pump bodies separated from each other and fluidly connected to each other by a communication pipe line.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A pump for feeding a liquid for chromatography, comprising:
   first and second chambers;
   first and second plungers forming first and second volumes respectively together with the first and second chambers and being capable of reciprocating in the first and second chambers respectively in such a manner that the first and second volumes are variable in accordance with respective movements of the first and second plungers;
   a communication path connecting fluidly the first and second volumes to each other;
   an inlet path communicating fluidly with the first volume, from which inlet path the liquid to be fed is capable of being supplied into the first volume; and
   an outlet path communicating fluidly with the second volume, by which outlet path the liquid to be fed is capable of being discharged from the second volume;
   wherein the first plunger is prevented from changing the first volume sufficiently for feeding the liquid between the first volume and the second volume when the second plunger decreases the second volume to discharge the fluid from the second volume to the outlet path for the chromatography; and
   wherein the first plunger is prevented from being moved during a time period which is greater than zero while the second plunger moves to decrease the second volume so that the fluid for the chromatography is discharged from the second volume.

2. A pump according to claim 1, wherein the first plunger is prevented from changing the first volume sufficiently for changing a pressure of the liquid in the second volume through the communication path when the second plunger decreases the second volume to discharge the fluid from the second volume to the outlet path for the chromatography.

3. A pump according to claim 1, wherein the communication path connects fluidly the first and second volumes to each other in series so that the liquid to be fed for the chromatography is capable of being fed from the first volume through the communication path to the second volume, the communication path includes a check valve for allowing the liquid to flow from the first volume into the second volume when a pressure in the first volume is higher than a pressure in the second volume and preventing the liquid from flowing from the second volume into the first volume when the pressure in the first volume is not higher than the pressure in the second volume.

4. A pump according to claim 3, wherein the check valve is capable of allowing the liquid to flow from the first volume into the second volume when the pressure in the first volume is higher than the pressure in the second volume and a difference in absolute value between the pressure in the first volume and the pressure in the second volume is more than a predetermined value more than zero, and of preventing the liquid from flowing from the first volume into the second volume when the pressure in the first volume is not higher than a total amount of the pressure in the second volume and the predetermined value.

5. A pump according to claim 4, wherein the first plunger is prevented from decreasing the first volume sufficiently for increasing the pressure of the liquid in the first volume to more than the total amount of the pressure in the second volume and the predetermined value when the second plunger decreases the second volume to discharge the fluid from the second volume to the outlet path for the chromatography.

6. A pump according to claim 1, wherein when the second plunger increases the second volume, the first plunger is capable of decreasing the first volume sufficiently for feeding the liquid from the first volume into the second volume.

7. A pump according to claim 6, wherein a difference between (a) a difference between (i) the increasing rate of the second volume increased by the second plunger and (ii) the decreasing rate of the volume of the first volume decreased by the first plunger and (b) a predetermined degree is kept within a predetermined range.

8. A pump according to claim 6, wherein a decreasing rate in absolute value of the first volume decreased by the first plunger is more than an increasing rate in absolute value of the second volume increased by the second plunger, and the movement of at least one of the first and second plungers is controlled in such a manner that a difference between (a) a difference in absolute value between (i) an increasing rate of the second volume increased by the second plunger and (ii) a decreasing rate of the volume of the first volume decreased by the first plunger and (b) a desired flow rate of the liquid to be discharged from the second volume to the outlet path for the chromatography is kept within a predetermined range.

9. A pump according to claim 1, wherein a change rate in absolute value of the first volume with respect to a movement velocity in absolute value of the first plunger is larger than a change rate in absolute value of the second volume with respect to a movement velocity in absolute value of the second plunger.

10. A pump according to claim 1, wherein the first plunger is capable of being stationary at least temporarily when the second plunger decreases the second volume to discharge the fluid from the second volume to the outlet path for the chromatography.

11. A pump according to claim 1, wherein a maximum change rate in absolute value of the first volume obtainable in accordance with the movement of the first plunger is larger than a maximum change rate in absolute value of the second volume obtainable in accordance with the movement of the second plunger, and a minimum change rate in absolute value of the first volume obtainable in accordance with the movement of the first plunger is smaller than the maximum change rate in absolute value of the second volume obtainable in accordance with the movement of the second plunger.

12. A pump for feeding a liquid for chromatography, comprising:
   first and second chambers;
   first and second plungers forming first and second volumes respectively together with the first and second chambers and being capable of reciprocating in the first and second chambers respectively in such a manner that the first and second volumes are variable in accordance with respective movements of the first and second plungers;
a communication path connecting fluidly the first and second volumes to each other;
an inlet path communicating fluidly with the first volume, from which inlet path the liquid to be fed is capable of being supplied into the first volume; and
an outlet path communicating fluidly with the second volume, by which outlet path the liquid to be fed is capable of being discharged from the second volume;
wherein the first plunger is prevented from changing the first volume sufficiently for feeding the liquid between the first volume and the second volume when the second plunger decreases the second volume to discharge the fluid from the second volume to the outlet path for the chromatography;
wherein the first plunger is prevented from being moved during a time period which is greater than zero while the second plunger moves to decrease the second volume so that the fluid for the chromatography is discharged from the second volume; and
wherein a movement velocity in absolute value of the second plunger for increasing the second volume is larger than a movement velocity in absolute value of the second plunger for decreasing the second volume to discharge the fluid from the second volume to the outlet path for the chromatography.

13. A pump according to claim 1, wherein the first plunger is capable of decreasing the first volume to increase a pressure in the first volume when the second plunger decreases the second volume.

14. A pump according to claim 1, wherein the first plunger is capable of decreasing the first volume to pressurize the fluid in the first volume to a pressure insufficient for feeding the liquid from the first volume into the second volume and not more than a desired pressure of the liquid to be discharged from the pump, when the second plunger decreases the second volume.

15. A pump according to claim 1, wherein the first plunger is prevented from being moved during the time period which is greater than zero, after the first plunger is moved to increase the pressure in the first volume to less than an opening pressure of a check valve between the first and second chambers.

16. A pump for feeding a liquid for chromatography, comprising:
first and second chambers;
first and second plungers forming first and second volumes respectively together with the first and second chambers and being capable of reciprocating in the first and second chambers respectively in such a manner that the first and second volumes are variable in accordance with respective movements of the first and second plungers;
a communication path connecting fluidly the first and second volumes to each other;
an inlet path communicating fluidly with the first volume, from which inlet path the liquid to be fed is capable of being supplied into the first volume; and
an outlet path communicating fluidly with the second volume, by which outlet path the liquid to be fed is capable of being discharged from the second volume;
wherein the first plunger is prevented from changing the first volume sufficiently for feeding the liquid between the first volume and the second volume when the second plunger decreases the second volume to discharge the fluid from the second volume to the outlet path for the chromatography;
wherein the first plunger is prevented from being moved during a time peroid which is greater than zero while the second plunger moves to decrease the second volume so that the fluid for the chromatography is discharged from the second volume;
wherein the communication path connects fluidly the first and second volumes to each other in series so that the liquid to be fed for the chromatography is capable of being fed from the first volume through the communication path to the second volume, the communication path includes a check valve for allowing the liquid to flow from the first volume into the second volume when a pressure in the first volume is higher than a pressure in the second volume and preventing the liquid from flowing from the second volume into the first volume when the pressure in the first volume is not higher than the pressure in the second volume;
wherein the check valve is capable of allowing the liquid to flow from the first volume into the second volume when the pressure in the first volume is higher than the pressure in the second volume and a difference in absolute value between the pressure in the first volume and the pressure in the second volume is more than a predetermined value more than zero, and of preventing the liquid from flowing from the first volume into the second volume when the pressure in the first volume is not higher than a total amount of the pressure in the second volume and the predetermined value;
wherein the first plunger is prevented from decreasing the first volume sufficiently for increasing the pressure of the liquid in the first volume to more than the total amount of the pressure in the second volume and the predetermined value when the second plunger decreases the second volume to discharge the fluid from the second volume to the outlet path for the chromatography; and
wherein when the second plunger decreases the second volume to discharge the fluid from the second volume to the outlet path for the chromatography, the first plunger is capable of decreasing the first volume to increase the pressure of the liquid in the first volume to more than a pressure in the inlet path and is prevented from decreasing the first volume sufficiently for increasing the pressure of the liquid in the first volume to more than the total amount of the pressure in the second volume and the predetermined value.

17. A pump according to claim 16, wherein when the second plunger decreases the second volume to discharge the fluid from the second volume to the outlet path for the chromatography, the first plunger is capable of decreasing the first volume to increase the pressure of the liquid in the first volume to more than the pressure in the second volume and is prevented from decreasing the first volume sufficiently for increasing the pressure of the liquid in the first volume to more than the total amount of the pressure in the second volume and the predetermined value.

18. A pump for feeding a liquid for chromatography, comprising:
first and second chambers;
first and second plungers forming first and second volumes respectively together with the first and second chambers and being capable of reciprocating in the first and second chambers respectively in such a manner that the first and second volumes are variable in accordance with respective movements of the first and second plungers;
a communication path connecting fluidly the first and second volumes to each other;
an inlet path communicating fluidly with the first volume, from which inlet path the liquid to be fed is capable of being supplied into the first volume; and
an outlet path communicating fluidly with the second volume, by which outlet path the liquid to be fed is capable of being discharged from the second volume;
wherein the first plunger is prevented from changing the first volume sufficiently for feeding the liquid between the first volume and the second volume when the second plunger decreases the second volume to discharge the fluid from the second volume to the outlet path for the chromatography;
wherein the first plunger is prevented from being moved during a time period which is greater than zero while the second plunger moves to decrease the second volume so that the fluid for the chromatography is discharged from the second volume;
wherein the communication path connects fluidly the first and second volumes to each other in series so that the liquid to be fed for the chromatography is capable of being fed from the first volume through the communication path to the second volume, the communication path includes a check valve for allowing the liquid to flow from the first volume into the second volume when a pressure in the first volume is higher than a pressure in the second volume and preventing the liquid from flowing from the second volume into the first volume when the pressure in the first volume is not higher than the pressure in the second volume; and
wherein when the second plunger decreases the second volume to discharge the fluid from the second volume to the outlet path for the chromatography, the first plunger is capable of decreasing the first volume to increase the pressure of the liquid in the first volume to more than a pressure in the inlet path and is prevented from decreasing the first volume sufficiently for increasing the pressure of the liquid in the first volume to more than the pressure in the second chamber.

19. A pump according to claim 18, wherein the check valve is capable of allowing the liquid to flow from the first volume into the second volume when the pressure in the first volume is more than the pressure in the second volume and a difference in absolute value between the pressure in the first volume and the pressure in the second volume is more than a predetermined value more than zero, and prevents the liquid from flowing from the first volume into the second volume when the pressure in the first volume is not more than a total amount of the pressure in the second volume and the predetermined value.

20. A pump for feeding a liquid for chromatography, comprising:
first and second chambers;
first and second plungers forming first and second volumes respectively together with the first and second chambers and being capable of reciprocating in the first and second chambers respectively in such a manner that the first and second volumes are variable in accordance with respective movements of the first and second plungers;
a communication path connecting fluidly the first and second volumes to each other;
an inlet path communicating fluidly with the first volume, from which inlet path the liquid to be fed is capable of being supplied into the first volume; and
an outlet path communicating fluidly with the second volume, by which outlet path the liquid to be fed is capable of being discharged from the second volume;
wherein the first plunger is prevented from changing the first volume sufficiently for feeding the liquid between the first volume and the second volume when the second plunger decreases the second volume to discharge the fluid from the second volume to the outlet path for the chromatography; and
wherein the outlet path includes a drain valve openable to discharge a gas out of the outlet path through the drain valve to fill the outlet path with the liquid when the first plunger decreases the first volume, and closable to discharge the fluid from the second volume out of the pump through the outlet path for the chromatography when the second plunger decreases the second volume.

21. A pump for feeding a liquid for chromatography, comprising:
first and second chambers;
first and second plungers forming first and second volumes respectively together with the first and second chambers and being capable of reciprocating in the first and second chambers respectively in such a manner that the first and second volumes are variable in accordance with respective movements of the first and second plungers;
a communication path connecting fluidly the first and second volumes to each other;
an inlet path communicating fluidly with the first volume, from which inlet path the liquid to be fed is capable of being supplied into the first volume; and
an outlet path communicating fluidly with the second volume, by which outlet path the liquid to be fed is capable of being discharged from the second volume;
wherein the first plunger is prevented from changing the first volume sufficiently for feeding the liquid between the first volume and the second volume when the second plunger decreases the second volume to discharge the fluid from the second volume to the outlet path for the chromatography;
wherein the first plunger is prevented from being moved while the second plunger moves to decrease the second volume so that the fluid for the chromatography is discharged from the second volume; and
wherein the first plunger moves to decrease the first volume in response to the second plunger reaching a front end of a moving stroke of the second plunger.

* * * * *